United States Patent
Bungo

[11] Patent Number: 5,920,389
[45] Date of Patent: Jul. 6, 1999

[54] MULTI-CHANNEL SPECTRO-PHOTOMETERS

[75] Inventor: Hajime Bungo, Kyoto, Japan

[73] Assignee: Shimadzu Corporation, Kyoto, Japan

[21] Appl. No.: 08/949,212

[22] Filed: Oct. 10, 1997

Related U.S. Application Data

[63] Continuation of application No. 08/713,233, Sep. 12, 1996, abandoned.

[30] Foreign Application Priority Data

Nov. 27, 1995 [JP] Japan .................................. 7-307503

[51] Int. Cl.$^6$ ...................................................... G01J 3/42
[52] U.S. Cl. ............................................................ 356/325
[58] Field of Search ..................... 356/324, 325, 356/326, 328, 308, 330–334, 319, 307

[56] References Cited

U.S. PATENT DOCUMENTS

| | | | |
|---|---|---|---|
| 4,158,505 | 6/1979 | Mathisen et al. | |
| 4,758,085 | 7/1988 | Leqime et al. | |
| 4,958,928 | 9/1990 | Kuderer | 356/328 |
| 5,517,302 | 5/1996 | Stearns et al. | 356/326 |
| 5,565,983 | 10/1996 | Barnard | 356/328 |

*Primary Examiner*—K P Hantis
*Attorney, Agent, or Firm*—Majestic, Parsons, Siebert & Hsue P.C.

[57] ABSTRACT

A multi-channel type spectro-photometer not only has a light source, a sample cell to which light from the light source is directed, a spectrometer to which light transmitting through the sample cell is directed, and an array of photo-diodes to which dispersed light from the spectrometer is directed, but also allows the user to specify a range of wavelength within which measurements are to be taken. An optimum charge-accumulating time during which charge is to be accumulated on the photo-diodes array is automatically set according to the range specified by the user. Alternatively, quantity of light received by the photo-diode array may be detected and an optimum charge-accumulating time may be automatically set according to the measured light intensity on the photo-diode array. Dark current and background measurements are taken before a sample is injected into the sample cell and transmitted light therethrough is measured to obtain the absorption spectrum of the sample.

7 Claims, 8 Drawing Sheets

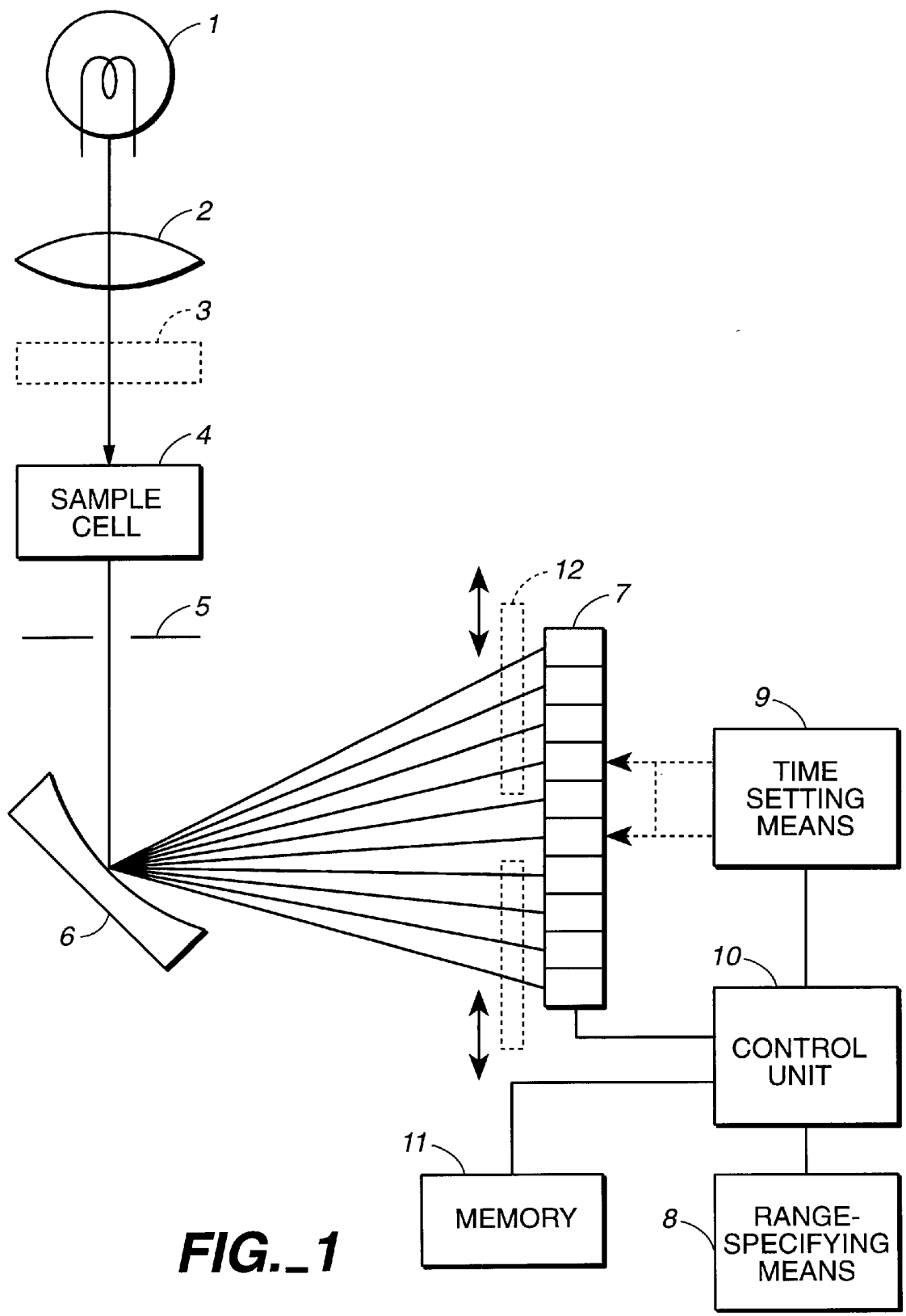
FIG._1

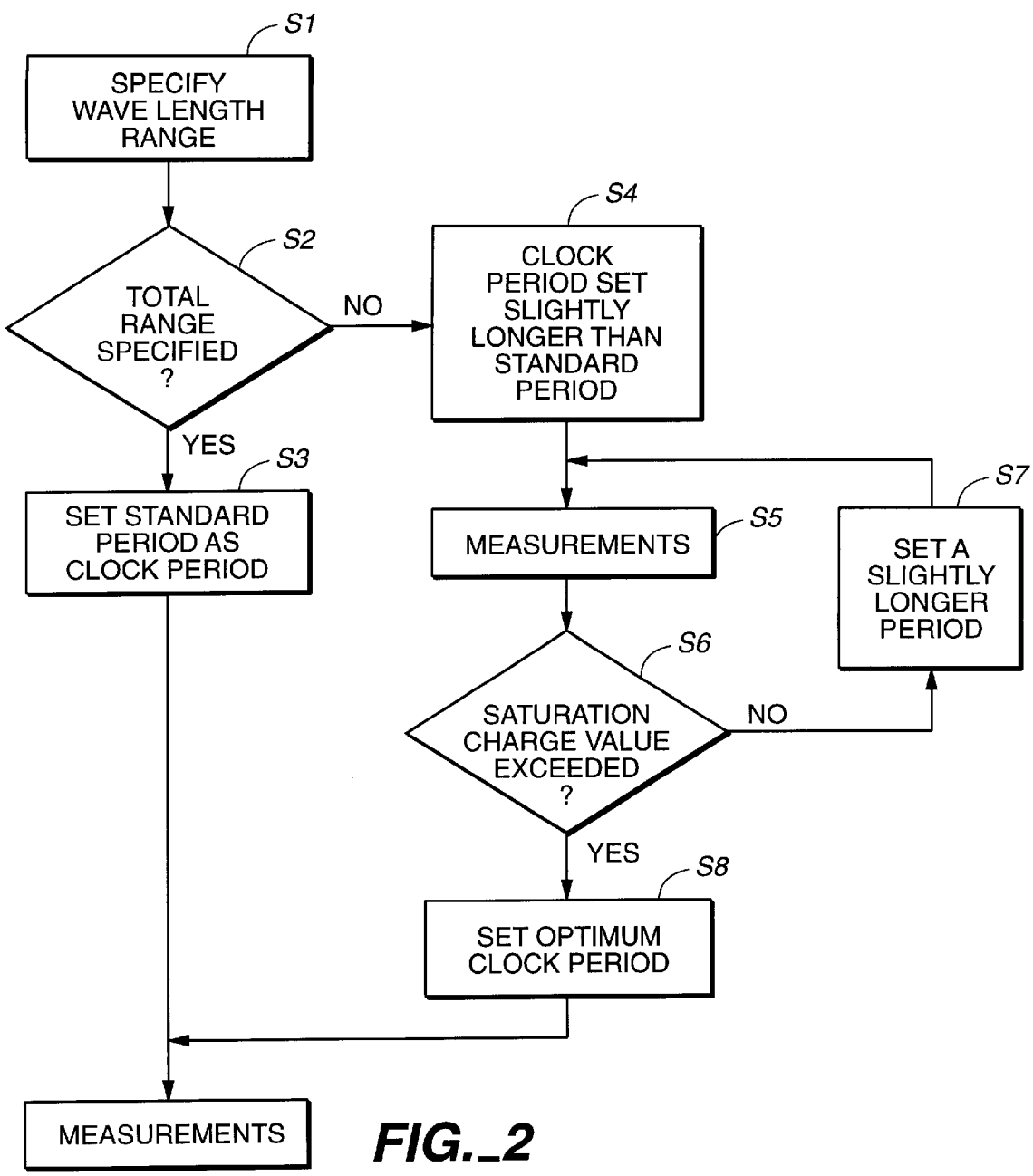
FIG._2

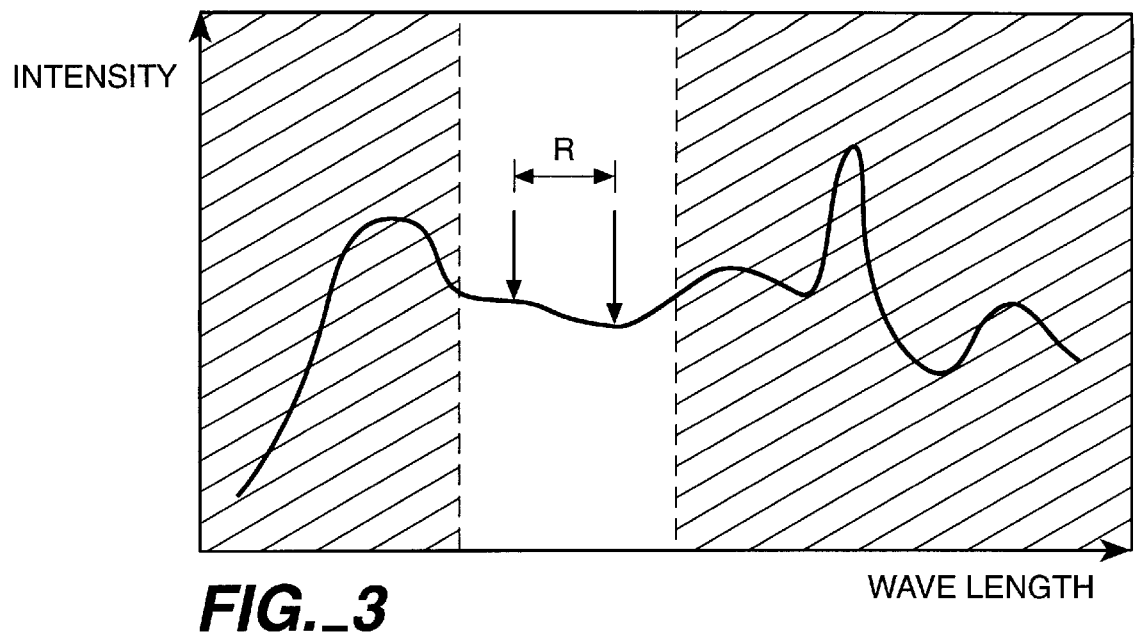
FIG._3
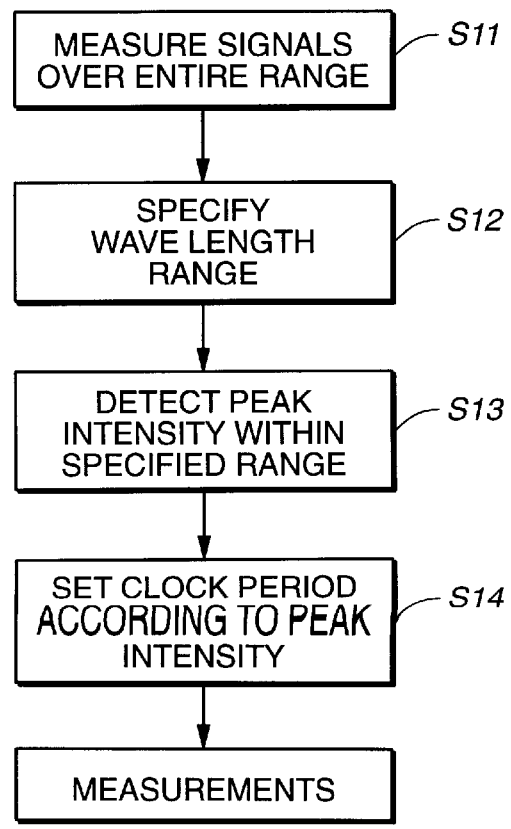
FIG._4

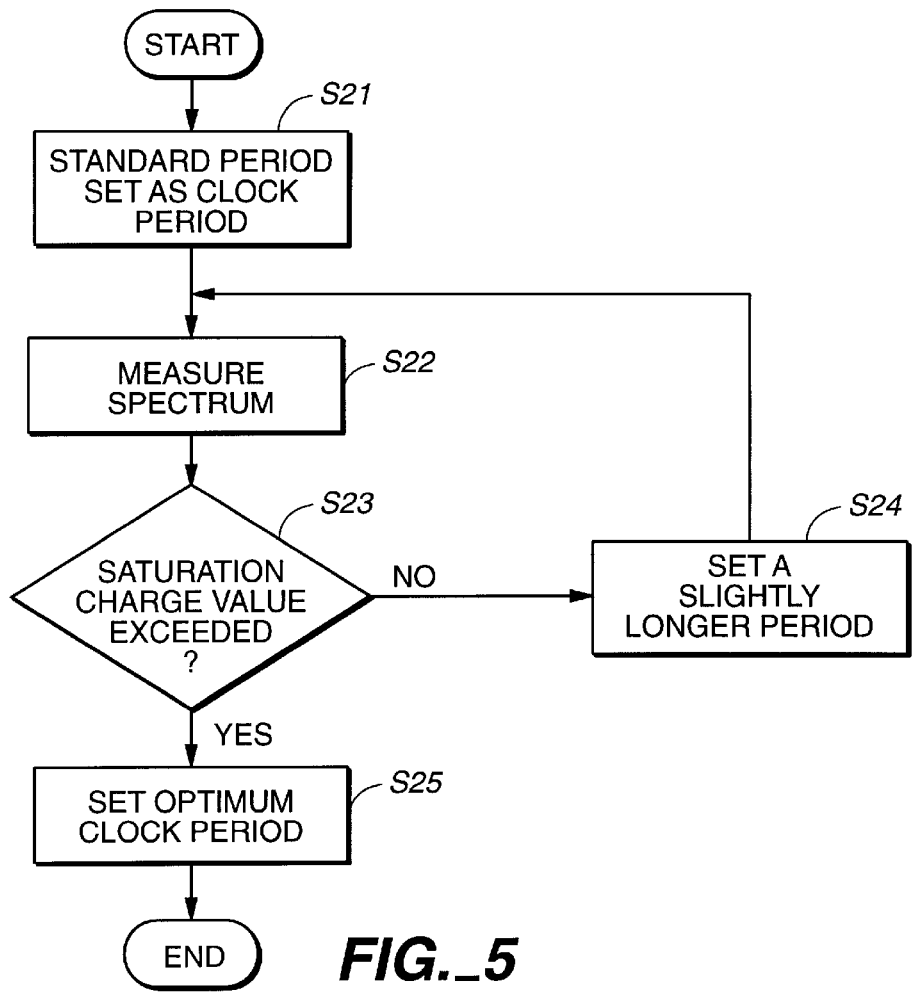
*FIG._5*
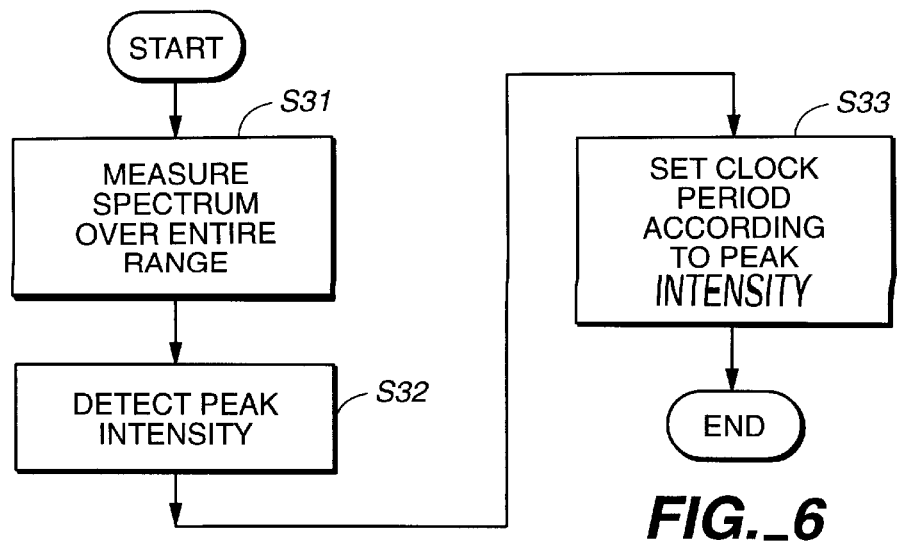
*FIG._6*

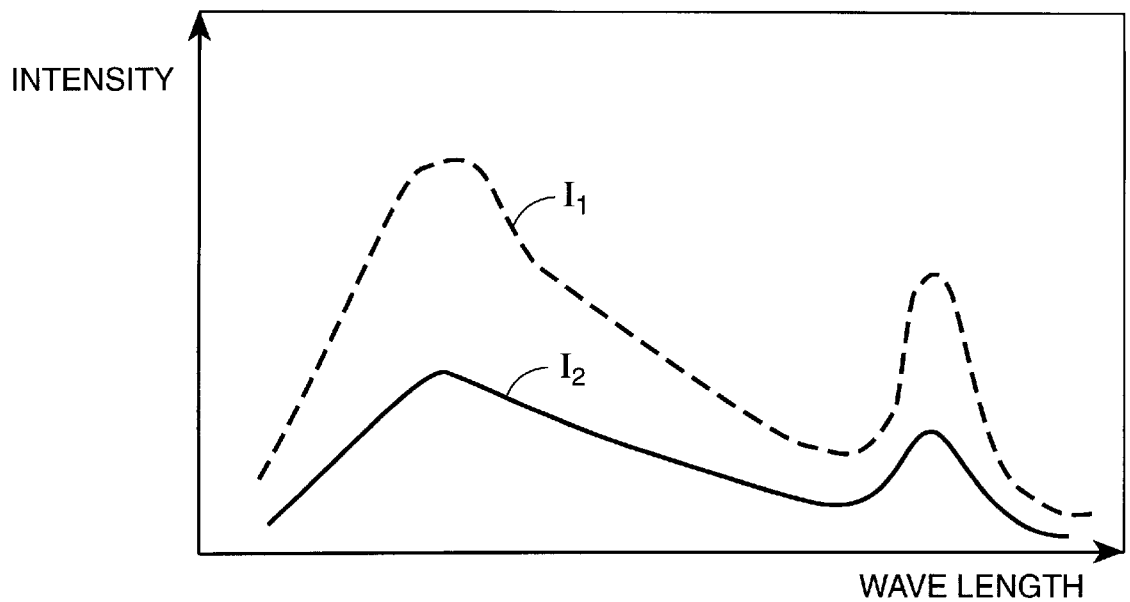
FIG._7
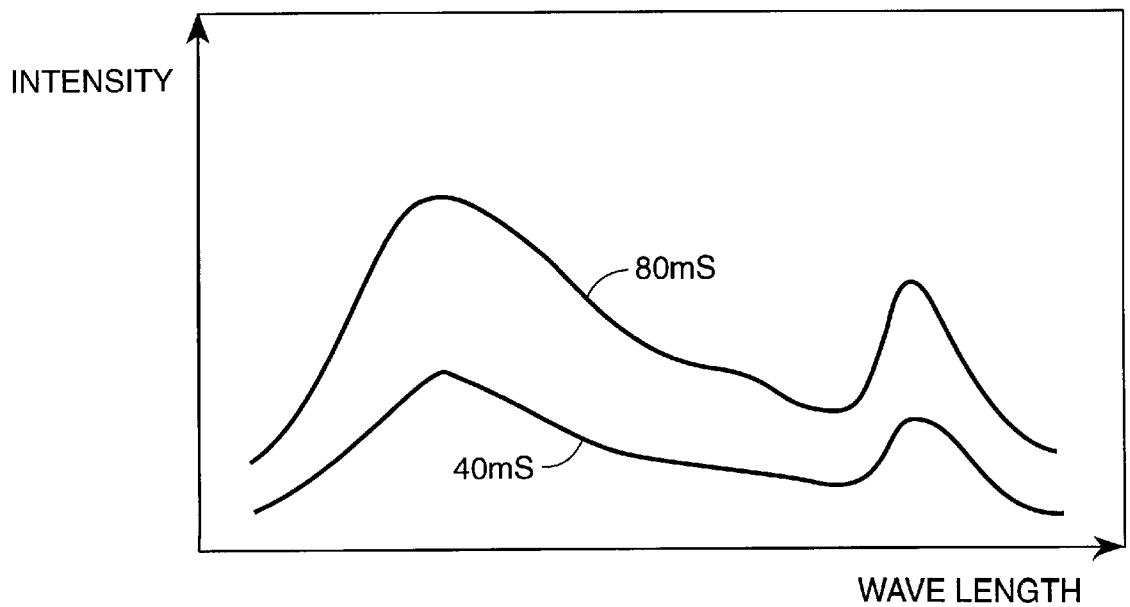
FIG._8

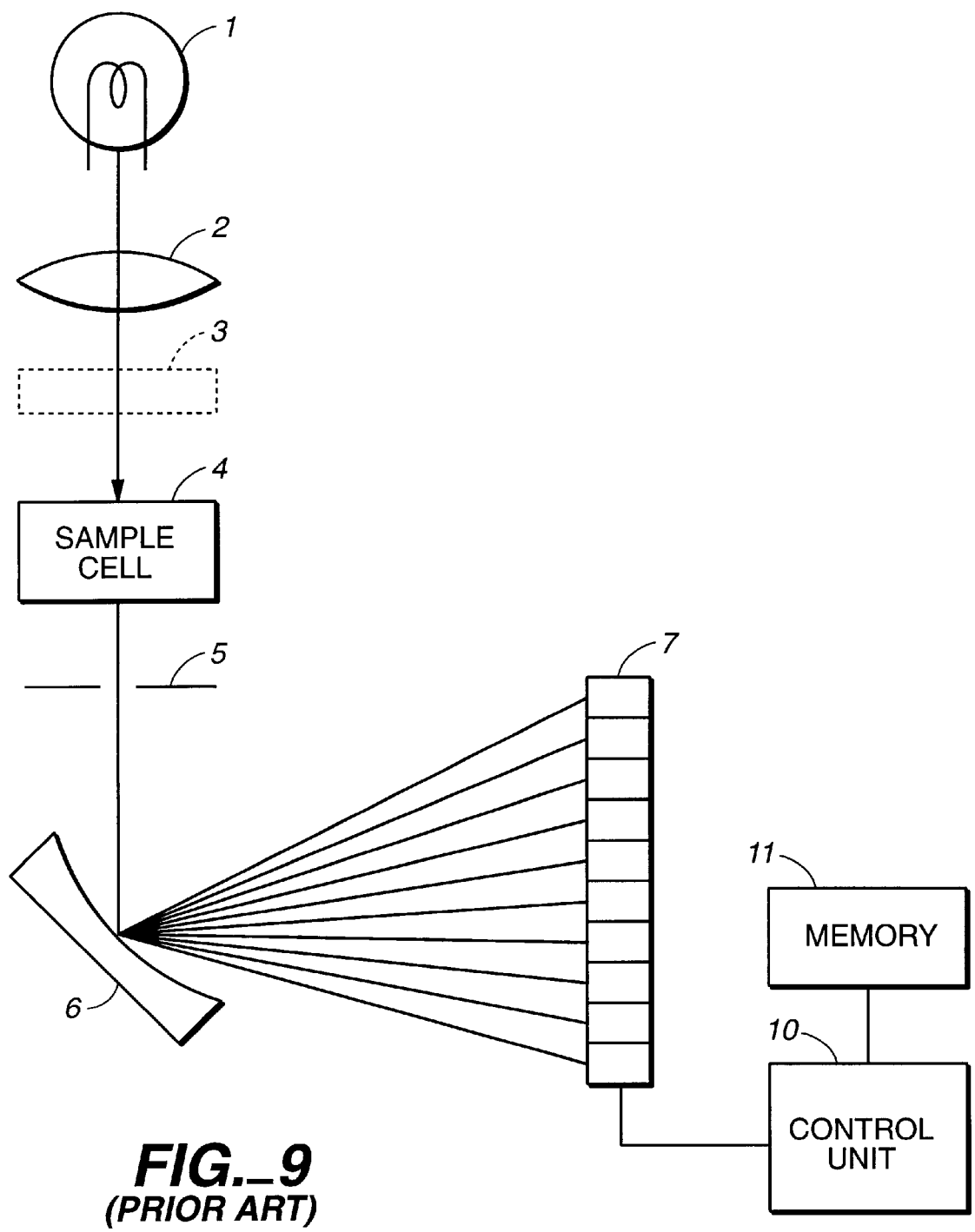
FIG._9
*(PRIOR ART)*

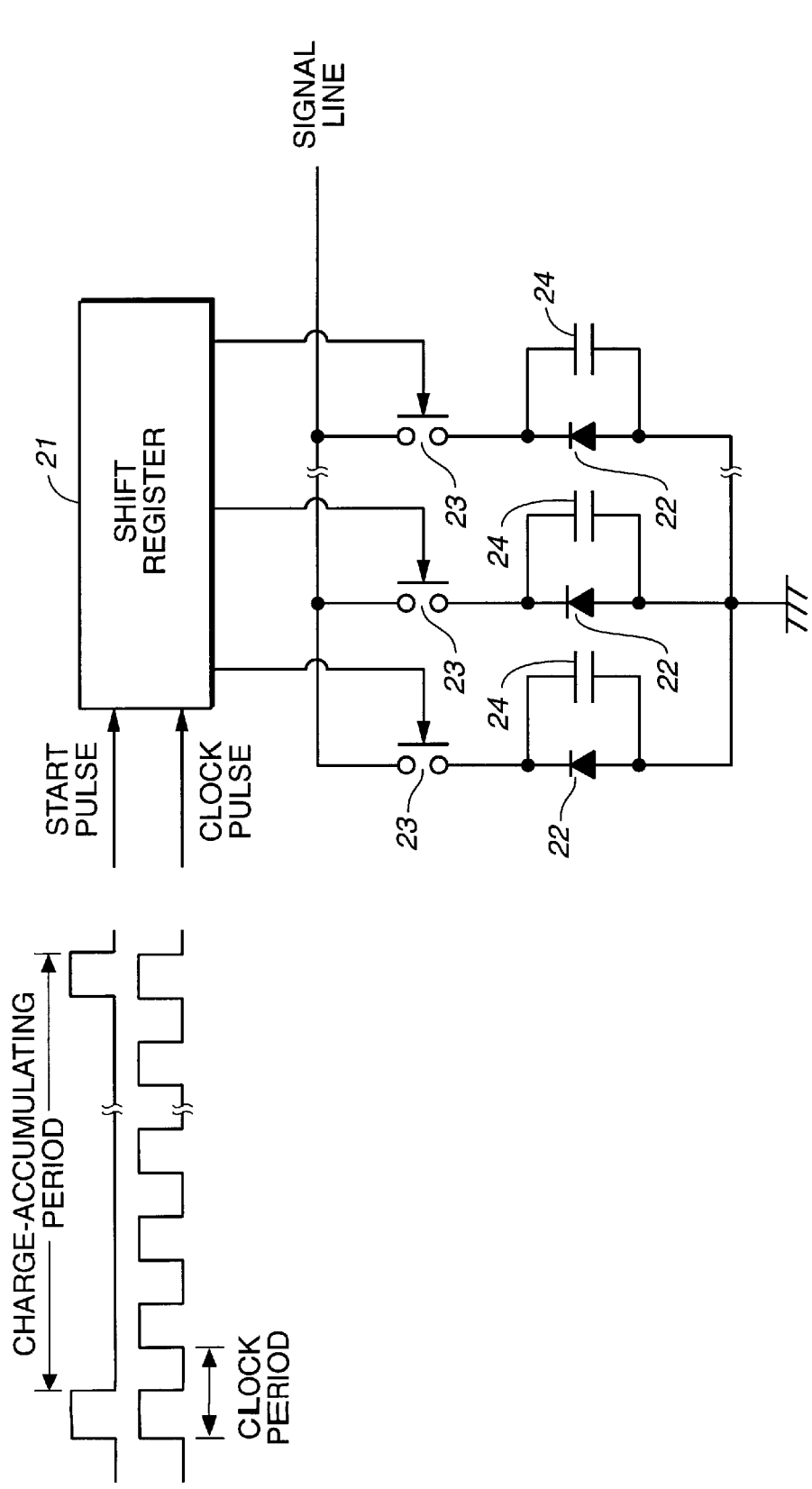
FIG._10 (PRIOR ART)

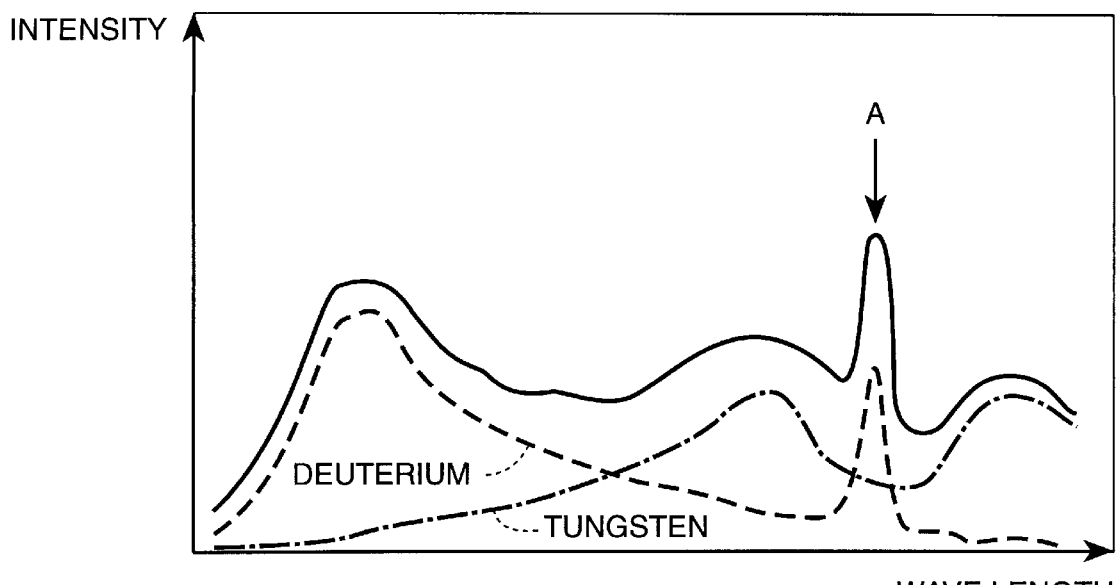
FIG._11 *(PRIOR ART)*
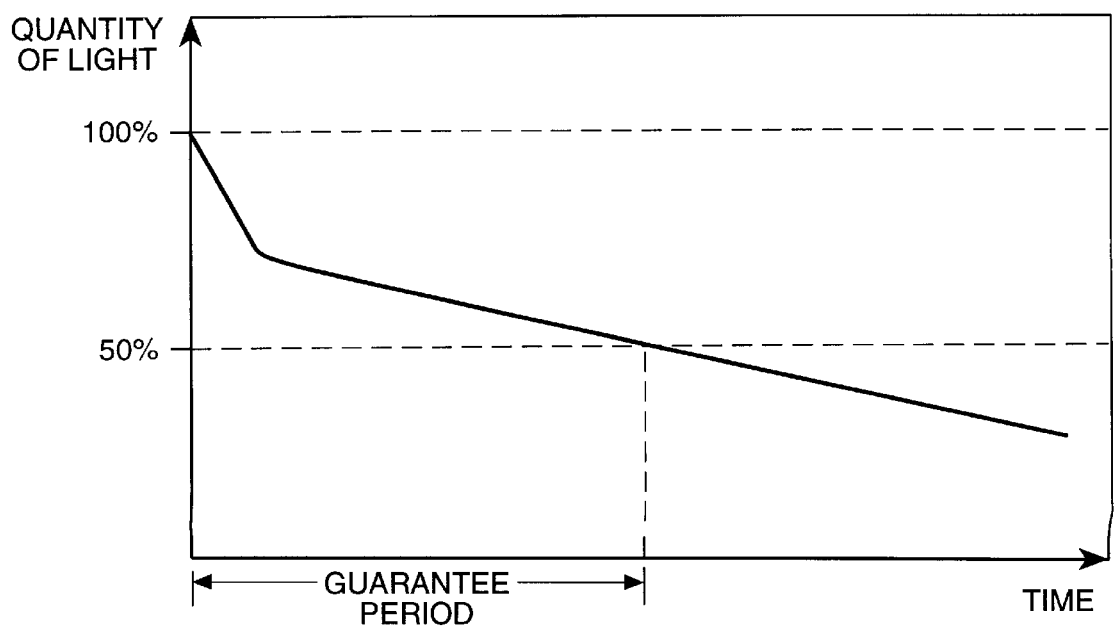
FIG._12 *(PRIOR ART)*

5,920,389

MULTI-CHANNEL SPECTRO-PHOTOMETERS

This is a continuation of application Ser. No. 08/713,233 filed Sep. 12, 1996, now abandoned.

BACKGROUND OF THE INVENTION

This invention relates to spectro-photometers adapted to be used as a multi-purpose spectro-photometer or a detector for a liquid chromatograph. More particularly, this invention relates to multi-channel type spectro-photometers having an array of photo-diodes as a detector.

The basic structure of a prior art multi-channel type spectro-photometer provided with an array of photo-diodes will be explained first with reference to FIG. 9, as comprising a light source 1, a sample cell 4, a converging lens 2 for collecting light from the light source 1 and guiding it to the sample cell 4, a shutter 3, a slit 5 at the entrance to a spectroscope, a concave grating 6 serving as the light-dispersing element of the spectroscope, a photo-diode array 7 disposed at the exit of the spectroscope to serve as a multi-channel detector, a signal processing and control circuit 10 (herein referred to as the control unit) and a memory 11. The concave grating 6 is adapted not only to disperse the light transmitted through the sample cell 4 but also to focus the image of the slit 5 on the light-receiving surface of the photo-diode array 7. The photo-diode array 7 may comprise, for example, 500 aligned light-receiving elements such that the light with wavelength 200 nm transmitted through the sample cell 4 will be received by the first light-receiving element on the light-receiving surface of the photo-diode array 7, that the light with wavelength 700 nm will be received by the 500th light-receiving element and that light with wavelength within the range of 200 nm to 700 nm can be detected by the elements therebetween. The shutter 3 is for carrying out dark current adjustments of the photo-diode array 7. When a dark current adjustment is carried out, the shutter 3 is closed to provide a dark condition, and the photo-diode array 7 is scanned by means of a driving circuit (not shown) to measure the dark current value of each light-receiving element, and the measured dark current values are stored in the memory 11. Next, the shutter 3 is opened to introduce light in order to determine the background condition of the absorption spectrum. The photo-diode array 7 is scanned to measure the signal from each light-receiving element, and the background spectrum is obtained by subtracting the dark current value of each light-receiving element from the measured value. The background spectrum thus obtained is also stored in the memory 11.

Next, a sample is injected into the sample cell 4, the shutter 3 is opened, and the light from the light source 1 is focused by the converging lens 2 and led to the sample cell 4. The light transmitted through the sample cell 4 is passed through the slit 5 and dispersed by the concave grating 6 such that the image of the slit 5 is on the surface of the photo-diode array 7. The photo-diode array 7 is scanned under this condition, and the signal from each light-receiving element is inputted to the control unit 10 for effecting dark current and background corrections to obtain the absorption spectrum of the sample.

The photo-diode array 7 may be structured as shown in FIG. 10 wherein numeral 21 indicates a shift register, numerals 22 indicate photo-diodes in the array 7, numerals 24 indicate capacitors each connected in parallel with an associated one of the photo-diodes 22, and numerals 23 indicate switches each connected in series with an associated one of the parallel connections of a photo-diode 22 and a capacitor 24. If light is made incident on each of the photo-diodes 22 while each of the capacitors 24 is in a charged condition, the capacitors 24 are discharged by the photoelectric effect. If the shift register 21 switches on the switches 23 sequentially one at a time at the frequency of a clock pulse as shown schematically in FIG. 10 and the electric charge on each capacitor 24 is measured, one can obtain the electric charge discharged from each capacitor 24. By repeating this measurement, one can obtain the amount of light which was made incident on each photo-diode 22 from the measured electric charge.

Prior art spectro-photometers of the multi-channel type were structured as explained above, and the series of measurements by the photo-diode array was controlled by the start pulse and the clock pulse as shown in FIG. 10, and the periods of these two pulses were set such that none of the elements would exceed the saturation charge value, or the limit value of discharge. In the case of a liquid chromatograph, for example, use may be made of both a deuterium lamp and a tungsten lamp as light source in order to cover a wide range of wavelength. Since the emission spectra of these two lamps are as shown in FIG. 11 by dotted and chain lines, respectively, and since these two lamps are turned on together, the total emission spectrum is as shown by the solid line in FIG. 11. In other words, the intensity varies significantly within the useful range of wavelength. As explained above, however, every light-receiving element of the photo-diode is exposed to light for a same period of time, while the saturation charge of photoelectric converter elements of a charge-accumulating type is finite. In order to prevent saturation, the time for charge accumulation must be limited. In the example of FIG. 11, the wavelength at which the intensity is the strongest is indicated by arrow A, and the charge-accumulating time is limited according to this maximum intensity. On the other hand, major sources of noise for photo-diodes are circuit noise and reset noise, but their magnitudes are constant, independent of the signal intensity. Thus, if the charge-accumulating time period is set such that there will be no saturation at the wavelength corresponding to the largest intensity within the range of wavelength of the light source, signals with wavelengths corresponding to smaller light intensities will be too small compared to the noise.

The sensitivity of a spectro-photometer as described above deteriorates with time because the quantity of light emitted from its light source decreases, as shown in FIG. 12 for a deuterium lamp. For this reason, a guarantee period is normally specified for each lamp, as indicated in FIG. 12, such that the user will be sure to exchange the lamp after its guarantee period has been exceeded. For a deuterium lamp, the guarantee period is about 2000 hours. If such a deuterium lamp is used for 8 hours every day, for example, it must be replaced within less than a year.

The sensitivity of such a spectro-photometer deteriorates also due to a change in the optical system such as when the slit is made narrower and the quantity of incident light is thereby reduced. In the case of a photometer using a tungsten lamp and a deuterium lamp as described above with reference to FIG. 11, its sensitivity will drop, for example, if only the tungsten lamp is used for measurements because the total quantity of light drops (from the solid line to the chain line as shown in FIG. 11).

SUMMARY OF THE INVENTION

It is therefore an object of this invention to provide a multi-channel type spectro-photometer capable of reducing the effects of noise as much as possible and allowing measurements with high sensitivity.

It is another object of this invention to provide such a multi-channel type spectro-photometer capable of keeping the effects of noise small even after its light source has deteriorated or if a change has been effected in its light source or its optical system.

It is still another object of this invention to provide such a multi-channel type spectro-photometer capable of significantly extending the useful lifetime of its lamp.

A multi-channel type spectro-photometer embodying this invention, with which the above and other objects can be accomplished, may be characterized as comprising not only a light source, a sample cell to which light from the light source is directed, a spectrometer to which light transmitting through the sample cell is directed, and an array of photo-diodes to which dispersed light from the spectrometer is directed but also range-specifying means for allowing the user to specify a range of wavelength and time-setting means for automatically setting a time period during which charge is to be accumulated on the photo-diodes according to the range specified through the range-specifying means.

With a spectro-photometer thus structured, the user may specify an appropriate range of wavelength and an optimum clock period is automatically determined for accumulation of charges for the photo-diode array such that measurements can be taken with high accuracy.

Alternatively, the spectro-photometer embodying the invention may comprise light-measuring means for measuring the quantity of light received by the photo-diode array and time-setting means for automatically determining and setting an optimum clock period according to the results of measurement by the light-measuring means.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic block diagram of a multi-channel type spectro-photometer embodying this invention;

FIG. 2 is a flow chart of a process for setting a clock period;

FIG. 3 is a graph, showing the effect of protective shutters on the spectrum of the light source of FIG. 1;

FIG. 4 is a flow chart of another process for setting clock period;

FIGS. 5 and 6 are flow charts of still other processes;

FIG. 7 shows a change in wavelength-intensity characteristic of a deuterium lamp with time;

FIG. 8 shows a change in wavelength-intensity characteristic due to a change in charge-accumulating time;

FIG. 9 is a schematic block diagram of a prior art multi-channel type spectro-photometer;

FIG. 10 is a schematic block diagram of the prior art photo-diode array shown in FIG. 9 with a timing chart for pulses received by the shift register;

FIG. 11 is a graph showing the spectrum of a light source having a tungsten lamp and a deuterium lamp; and FIG. 12 is a graph showing the deterioration with time of a deuterium lamp.

Throughout herein, those components that are substantially identical, although they may be components of different devices, are indicated by the same numeral and may not be explained repetitively.

DETAILED DESCRIPTION OF THE INVENTION

As shown in FIG. 1, a multi-channel type spectro-photometer embodying this invention comprises a light source 1, a sample cell 4, a converging lens 2 for collecting light from the light source 1 and guiding it to the sample cell 4, a shutter 3, a slit 5 at the entrance to a spectroscope, a concave grating 6 serving as the light-dispersing element of the spectroscope, a photo-diode array 7 disposed at the exit of the spectro-scope to serve as a multi-channel detector, a means for specifying a wavelength range 8 (or the range-specifying means), a means for setting charge-accumulating time (or, the time-setting means) 9 for each of the photo-diodes of the array 7 as indicated schematically by dotted arrows, a signal processing and control circuit ("the control unit") 10, a memory 11 and protective shutters 12. Those of the components that are substantially identical to those explained above with reference to FIG. 9 are indicated by the same numerals for convenience.

Next, the operation of the spectro-photometer of FIG. 1 is explained with reference to FIGS. 2, 3 and 10. First, the user specifies, through the range-specifying means 8, a range R of wavelength within which measurements are to be taken (Step S1), and the control unit 10 determines whether this specified range R is the total range of wavelength of the light source 1 or not (Step S2). If it is the total range (YES in Step S2), the clock period corresponding to the charge-accumulating time limited as explained above to prevent saturation in view of the intensity distribution as shown in FIG. 11 (referred to as the "standard period") is set in the time-setting means 9 as the clock period (Step S3).

If the specified range R is less than the total range of wavelength (NO in Step S2), measurements are taken (Step S5) after a time period which is somewhat longer than the aforementioned standard period corresponding to the standard charge-accumulating time is set in the time-setting means 9 by the control unit 10 (Step S4). In this measurement process (Step S5), the shutter 3 is first kept open without any sample inside the sample cell 4, and the shift register 21 is caused to switch on the switches 23 sequentially. The charges on the capacitors 24 connected individually to the photo-diodes 22 in parallel are thus measured sequentially and the charge values on the capacitors 24 are obtained. After a graph of intensity-wavelength characteristic (spectrum) is thus obtained, the control unit 10 determines whether the charge on any of the photo-diodes 22 exceeds the saturation charge value for the photo-diode array 7 or not (Step S6). If the charges on the photo-diodes 22 do not exceed the saturation value (NO in Step S6), the control unit 10 sets a somewhat longer clock period in the time-setting means 9 (Step S7), and the process in Step S5 is repeated. If any of the measured charge values exceeds the saturation value (YES in Step S6), the control unit 10 finally sets the previous clock period in the time-setting means 9 as the optimum clock period (Step S8).

After the optimum clock period is thus determined, the control unit 10 causes the shutter 3 to be closed to establish a dark condition. The dark currents of the photo-diodes 22 are measured, and the measured dark current values are stored in the memory 11. The control unit 10 next opens the shutter 3 in order to measure the background for the absorption spectrum, scans the photo-diode array 7 to measure their charge values, and obtains the background spectrum R(n) by subtracting the dark current values individually from the measured charge values (n being a dummy index representing each photo-diode or its corresponding wavelength). The background spectrum R(n) thus obtained is also stored in the memory 11.

Next, a sample is injected into the sample cell 4, the shutter 3 is kept in the open condition and the light from the light source 1 is projected on the sample cell 4. Transmitted light through the sample cell 4 is passed through the slit 5, scattered and dispersed by the concave grating 6, and focused so as to form an image of the slit 5 on the surface of the photo-diode array 7. Under this condition, the control unit 10 causes the photo-diode array 7 to be scanned to measure the discharges through the individual photo-diodes 22. Of these measured charge values, only the signals within the pre-set wavelength range are subjected to the dark current and background corrections, and the transmitted light signals S(n) from the sample are thus calculated and stored in the memory 11. The control unit 10 is further adapted to calculate the absorption spectrum A(n) of the sample as follows from the transmitted light signals S(n) and the previously obtained background spectrum R(n):

$$A(n) = -\log_{10}(S(n)/R(n)).$$

The protective shutters 12, provided in front of the photo-diode array 7, are adapted to move, as indicated by double-headed arrows, according to the specified range of wavelength such that those of the photo-diodes 22 corresponding to the wavelengths outside the specified range will be covered thereby. This is illustrated schematically in FIG. 3 wherein the hatched areas indicate the wavelengths corresponding to the photo-diodes 22 screened by the protective shutters 12 and hence not exposed to light. This is to prevent adverse effects on the photo-diodes if they remain exposed to strong light beyond the saturation value, thereby increasing the dark current. In cases where the dark current is small and no serious effect is to be expected from strong light, however, these protective shutters 12 need not be provided.

The invention has been described above with reference to only one example, but this example is not intended to limit the scope of the invention. Many modifications and variations are possible within the scope of the invention. For example, the "optimum clock period" need not necessarily be determined by the method of gradually increasing the clock period as the charge-accumulating time, as described above. Instead, this may be done by measuring the spectrum of the light source before the measurement with a sample and setting a clock period from a peak intensity value within the specified range R of wavelength.

In this mode of operation illustrated in FIG. 4, the control unit 10 opens the shutter 3, scans the photo-diode array 7 to measure the charge values of all individual photo-diodes 22 and stores the measured values in the memory 11 as the spectrum for the light source 1 for the entire range of wavelength (Step 11). The user is then required to input through the range-specifying means 8 a range of wavelength within which measurements are to be taken (Step S12), causing the control unit 10 to respond by determining the peak intensity from the measured signal intensity values stored in the memory 11 within the inputted range R of wavelength. The control unit 10 further calculates an optimum clock period not only in view of the standard period as defined above but also from the ratio between the peak intensity within the entire frequency range and the peak intensity within the inputted (specified) frequency range. The optimum clock period thus calculated is then set in the time-setting means 9.

After the optimum clock period is thus set in the time-setting means 9, the absorption spectrum of the sample is obtained as explained above by measuring the background first and effecting dark current and background corrections on the signals within the specified range of wavelength.

As a variation of the above, the shift register 21 may be controlled such that only the signals within the specified range of wavelength are retrieved from the photo-diodes 22, instead of retrieving all outputs from the photo-diode array 7 over the entire wavelength range, and that only those of the signals within the specified range of wavelength are processed.

FIG. 5 shows still another embodiment of this invention according to which the user does not specify any range of wavelength and hence the range-specifying means 8 or the protective shutters 12 of FIG. 1 are not required. According to this embodiment, the user starts a program for automatically setting an optimum charge-accumulating time. (The input means through which the user starts this program is not shown.) The control unit 10 responds by first setting in the time-setting means 9 the standard period as defined above as the clock period (Step S21). It then opens the shutter 3 without any sample inside the sample cell 4, causes the shift register 21 to switch on the switches 23 sequentially and thereby measures the charges on the charged capacitors 24 to determine the discharges from the individual capacitors 24 and to obtain the wavelength-intensity characteristic, or the spectrum (Step S22). After a graph of the intensity-wavelength characteristic (spectrum) is thus obtained, the control unit 10 determines whether the measured charge value associated with any of the photo-diodes 22 exceeds their saturation charge value or not (Step S23). If the measured charge values do not exceed the saturation value (NO in Step S23), the control unit 10 sets a somewhat longer clock period in the time-setting means 9 (Step S24), and the measurement in Step S22 is repeated. If any of the measured charge values exceeds the saturation value (YES in Step S23), the control unit 10 finally sets the previous clock period (that is, before the last increment) in the time-setting means 9 as the optimum clock period (Step S25). Thereafter, the absorption spectrum A(n) is calculated as described above with reference to FIG. 2.

Alternatively, the optimum clock period may be determined, as shown in FIG. 6, by measuring the spectrum of the light source before the sample measurement is started. According to this embodiment of the invention, the control unit 10 opens the shutter 3, scans the photo-diode array 7 to measure the charge values associated with all individual photo-diodes 22 and stores the measured values in the memory 11 as the spectrum for the light source 1 over the entire range of wavelength (Step 31). Next, the control unit 10 determines the peak intensity from the measured signal intensity values over the entire range of wavelength stored in the memory 11 (Step S32). The control unit 10 then calculates an optimum clock period from the standard period as defined above and the ratio between the peak intensity which was earlier obtained when, for example, the light source 1 was new (or after the light source 1 was most recently replaced) and the peak intensity value which was just obtained in Step S32 (Step S33). The optimum clock period thus calculated is then set in the time-setting means 9. Thereafter, as described above for the first embodiment of this invention, dark currents and background spectrum are measured, sample measurements are taken, and an absorption spectrum is calculated.

With a photometer according to this invention, if the wavelength-intensity characteristic of its light source has changed with time from Curve $I_1$ (dotted line) to Curve $I_2$ (solid line) in FIG. 7, quantity of light received by the photo-diode array is detected and the charge-accumulating time is automatically changed (say, from 40 ms to 80 ms) such that the wavelength-intensity characteristic can be changed as shown in FIG. 8. Thus, an optimum charge-accumulating time can be selected according to the quantity of incident light, and this makes it possible to minimize the effects of noise and to carry out high-sensitivity measurements.

The setting of charge-accumulating time as described above may be carried out either in response to a signal inputted by the user to start the program described above or automatically at a set frequency (or period). A new charge-accumulating time may also be set whenever a change is made to the light source or the optical system.

Although the invention has been described above as applied to a multi-purpose spectro-photometer, the invention may be equally well utilized as a detector for a liquid chromatograph by using a flow cell as the sample cell 4, causing the eluent from a column to flow into the flow cell and measuring the spectrum of light passing through the flow cell successively by the photo-diode array. Use may also be made of a concave mirror instead of the converging lens 2 to focus the light from the light source 1. All such modifications and variations that may be apparent to a person skilled in the art are intended to be within the scope of this invention.

What is claimed is:

1. A multi-channel type spectro-photometer comprising:
   a light source;
   a sample cell to which light from said light source is directed;
   a shutter disposed between said light source and said sample cell:
   an array of photo-diodes, a saturation value being associated with said photo-diodes;
   light dispersing means for receiving light transmitted through said sample cell and dispersing said received light to said photo-diodes;
   range-specifying means for allowing a user to specify a range of wavelength equal to or less than a total range;
   time-setting means for setting for each of said photo-diodes a charge-accumulating time during which charge is to be accumulated thereon; and
   a control means for causing said time-setting means to set a standard period if said total range is specified through said range-specifying means, said control means repeating a measurement process if less than said total range is specified through said range-specifying means, said measurement process comprising the steps of opening said shutter, with no sample being contained in said sample cell, to allow light from said light source to pass through said sample cell and to be received by said photo-diodes, measuring charges thereby accumulated on each of said photo-diodes, judging for each of said photo-diodes whether a charge in excess of said saturation value has been accumulated, and increasing the charge-accumulating time for each of those of the photo-diodes found not to have accumulated said saturation value of charge until a maximum charge-accumulation time is determined at which none of said photo-diodes accumulates a charge in excess of said saturation value.

2. The spectro-photometer of claim 1 wherein said control means serves to determine said standard clock time by the peak intensity of the spectrum of said light source, and to set an increasingly longer time than said standard period as said charge-accumulating time if less than said total range is specified through said range-specifying means until said photo-diodes are saturated.

3. The spectro-photometer of claim 1 further comprising:
   protective shutters disposed between said light dispersing means and said photo-diode array for screening said photo-diode array from portions of said dispersed light with wavelength not specified through said range-specified means.

4. The spectro-photometer of claim 1 wherein said control unit also serves to measure peak intensity of light with wavelength within a range specified through said range-specifying means and to determine said charge-accumulating time according to the measured peak intensity.

5. The spectro-photometer of claim 1 further comprising a memory device, said control means further serving to close said shutter to establish a dark condition, to measure dark currents of said photo-diodes under said dark condition, and to store measured values of said dark currents in said memory device.

6. The spectro-photometer of claim 5 wherein said control means further serves to open said shutter to establish an open condition, to measure charge values of said photo-diodes while said sample cell remains empty, to obtain a background spectrum under said open condition from said measured values of said dark currents and said measured charge values, and to store said background spectrum in said memory device.

7. The spectro-photometer of claim 6 wherein said control means further serves to subsequently cause light from said light source to be projected on a sample inside said sample cell, to cause said photo-diodes to be scanned so as to measure discharges through individual ones of said photo-diodes, and to calculate a transmitted light spectrum.

* * * * *